United States Patent
Kurosawa et al.

[11] Patent Number: 6,143,165
[45] Date of Patent: *Nov. 7, 2000

[54] NOX SENSOR

[75] Inventors: Hideyuki Kurosawa; Masaharu Hasei, both of Kumagaya; Noboru Yamazoe, Kasuga; Norio Miura, Fukuoka, all of Japan

[73] Assignee: Kabushiki Kaisha Riken, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/039,248

[22] Filed: Mar. 16, 1998

Related U.S. Application Data

[63] Continuation of application No. 08/712,376, Sep. 11, 1996, abandoned.

[30] Foreign Application Priority Data

Jul. 28, 1994 [JP] Japan ......................................... 194605

[51] Int. Cl.[7] .................................................. G01N 27/407
[52] U.S. Cl. ............................ 205/781; 204/424; 204/426
[58] Field of Search ..................................... 204/421–429; 205/781, 783, 783.5, 784, 784.5, 785

[56] References Cited

U.S. PATENT DOCUMENTS

| | | | |
|---|---|---|---|
| 4,126,532 | 11/1978 | Takao et al. | 204/195 |
| 4,345,985 | 8/1982 | Tohda et al. | 204/192 |
| 4,502,939 | 3/1985 | Holfelder et al. | 204/429 |
| 4,587,105 | 5/1986 | Bonne et al. | 422/98 |
| 4,770,760 | 9/1988 | Noda et al. | 204/425 |
| 5,034,112 | 7/1991 | Murase et al. | 204/425 |
| 5,037,525 | 8/1991 | Badwal | 204/421 |
| 5,217,588 | 6/1993 | Wang et al. | 205/781 |
| 5,397,442 | 3/1995 | Wachsman | 204/153.16 |
| 5,486,336 | 1/1996 | Betta et al. | 422/90 |

FOREIGN PATENT DOCUMENTS 61-184450  8/1986  Japan.

OTHER PUBLICATIONS

Shen Yao et al., "Use of Sodium Nitrite Auxiliary Electrode for Solid Electrolyte Sensor to Detect Notrogen Oxides", Chemistry Letters, pp. 587–590(1992) month unavailable.

Youichi Shimizu et al., "Solid Electrolyte $NO_2$ Sensors Fitted with Sodium Nitrate and/or Barium Nitrate Electrodes", Denki Kagaku, vol. 59, pp. 11–18 (1991) month unavailable.

Hideyuki Kurosawa et al., "Solid Electrolyte NOx Sensor Using Oxide Ion Conductor", The 18 Chemical Sensor Meeting, vol. 10, pp. 73–76 (1993) month unavailable.

Daniel Murphy, "Periodic Table of The Elements", Foundations of College Chemistry, 2nd Ed., the inside cover page (1975) month unavailable.

*Primary Examiner*—T. Tung
*Attorney, Agent, or Firm*—Kubovcik & Kubovcik

[57] ABSTRACT

The present invention discloses a NOx sensor consisting of at least a pair of electrodes formed in touch with an ion conductive solid electrolyte; wherein the first electrode is composed of oxides of a metal (Cr, Mo or W) selected from 6a Group or a substance containing said oxides and an electric conductive material and the concentration of NOx in the test gas is detected by the change of the electromotive force between the first and second electrodes.

2 Claims, 3 Drawing Sheets

NOX SENSOR

This application is a continuation of application Ser. No. 08/712,376, filed Sep. 11, 1996, now abandoned.

BACKGROUND OF THE INVENTION

1. Field of the Invention

The present invention relates to a sensor which detects NOx concentration in an exhaust gas from a combustion furnace, automobile engine, etc.

Currently, sensors based on a spectroscopic absorbance method, emission spectrochemical method, etc. are commercialized for the detection of NOx. However, based on these methodologies is large sized and expensive and also it takes a long time for the measurement due to its complexity of operation. Therefore, the development of a small sized and simple sensor is needed and a solid element sensor using a solid electrolyte has been proposed. The representative sensor hereto proposed is a semiconductor sensor which utilizes the fact that the electrical resistance of an oxide semiconductor changes by the existence of NOx gas or a solid electrolyte sensor which measures the equilibrium electromotive force caused by the difference of the partial presence of the gases on both sides of a separation wall.

In a solid electrolyte sensor, the selectivity and sensitivity are improved by the preparation of various kinds of nitrate electrode as a detecting electrode. For example, Japanese Patent Laid-open Publication No. Sho 61-184450 discloses a solid element sensor, wherein AgI or $RbAg_4I_5$ is used as a solid electrolyte and the other electrode is coated by silver nitrate. This sensor is a concentration cell type, wherein Ag ion in the nitrate migrates in the solid electrolyte by the difference of - NOx concentration between the electrodes and causes an electromotive force which complies with Nernst formula and detects NOx concentration by the measurement of said electromotive force. This type of sensor is sensitive to either $NO_2$ and NO, However the operation condition is limited because $AgNO_3$ is water soluble and its melting point is 212° C.

A concentration cell type sensor with high sensitivity to NO using NASICON ($Na_3Zr_2Si_2PO_{12}$) as a solid electrolyte and $NaNO_2$ as an electrode is disclosed in Chemistry Letters, vol.1, p.587~590 (1992). In this sensor, the working condition is limited due to the low melting point of $NaNO_2$, 217° C. and its deliquescence property.

As a sensor workable at comparatively higher temperature, a concentration cell using Na ion conductive β/β" alumina or β/β" alumina in which Na ion is replaced by Ba ion and using $Ba(NO_3)_2$ or a mixture of $NaNO_3$ and $Ba(NO_3)_2$ as an electrode is disclosed in Denki Kagaku, vol.59, (1991), p.465~472. In these sensors, wherein Na ion conductive β/β" alumina is used as a solid electrolyte and $Ba(NO_3)_2$ is used as an electrode, an electromotive force complying with the Nernst formula be obtained. In concentration cell type sensors wherein a mixture of $NaNO_3$ and $Ba(NO_3)_2$ is used and sensors, wherein β/β" alumina, in which Na ion is replaced by Ba ion and $Ba(NO_3)_2$, is used it is reported that electromotive force complying with Nernst formula is obtained. Since $Ba(NO_3)_2$ is a nitrate having higher melting point among nitrates, it is workable around 450° C., However, there are issues for the measurement in an atmosphere containing water vapor and in long term stability.

Zirconia is used in a commercialized oxygen sensor as a thermal stable electrolyte at a high temperature. In an NOx sensor using zirconia, it is reported that a good performance is obtained by using mixed salts of $Ba(NO_3)_2$ and or $Ba(NO_3)_2$ with other salts as an electrode. (The 18th Chemical Sensor Meeting, vol.10, p.73~76, 1993). However, long range stability is an issue due to the deliquescence property of $Ba(NO_3)_2$. A sensor using $SnO_2$ which is stable at a relatively high temperature as an electrode and zirconia as an electrolyte is reported, However, the detectable gas is methane, but not NOx.

Thus, in a solid element type sensor using a solid electrolyte having a sensitivity to NOx, its working temperature is limited due to the melting point of nitrate used as an electrode. The working condition has been limited due to the destruction of the function of the sensor caused by melting and decomposition of nitrates when exposed to a temperature above the melting point. Furthermore, it was not possible to detect NO because it has an enough sensitivity to $NO_2$, but almost no sensitivity to NO.

SUMMARY OF THE INVENTION

The present invention intends to provide a thermal resistant NOx sensor for the detection of NOx concentration, especially NO concentration in an exhaust gas from a combustion furnace and an automobile engine, having sufficient sensitivity to NO, workable at a temperature above 500° C. and having a sensor function at exposure to an atmosphere above 500° C.

The sensor of the present invention is an NOx sensor consisting at least of a pair of electrodes formed in contact with an ion conductive solid electrolyte, wherein at least the first electrode is composed of oxides of Group 6b metals or a substance containing said oxides to detect the electomotive force caused by a concentration difference of NOx between the electrodes.

DETAILED DESCRIPTION

Figure 1:
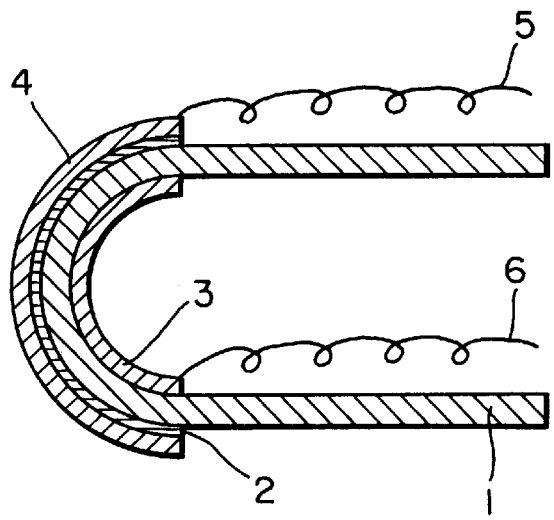
FIG. 1 shows a cross section of an example of a NOx sensor according to the present invention.

More concretely, an NOx sensor according to the present invention is composed of the combination of conductive materials functioning as a collector containing any one of a Group 6b metal, Cr, Mo and W.

These metal oxides are in various states such as $Cr_2O_3$, CrO, $CrO_3$, $MoO_2$, $MoO_3$, $WO_2$ and $WO_3$, and the state largely depends on the oxygen partial pressure and temperature. For this reason, an oxide such as $Cr_2O_3$, $MoO_3$ and $WO_3$, which are stable in an atmosphere containing oxygen at several hundreds ° C. temperature is preferred as the first electrode composed of any one of Cr, Mo and W, and the mixed metal oxide with different oxidation states also can be used as the first electrode.

And the composed electrode can be a kind of oxides of a metal selected from Cr, Mo and W or a mixture of more than two kinds of metal oxides. Furthermore, it can be a mixture of more than one kind of metal oxide with noble metals such as Au and Pt or with oxides of a metal other than a Group 6b which does not make a solution with an oxide of Cr, Mo and W. At least oxides of Cr, Mo and W must be contained in the first electrode.

A collector is laminated or mixed with the above mentioned oxide layer and rare metals or oxides having corrosion resistance property can be used as the material.

Oxygen ion conductive materials, zirconia ($ZrO_2$—$M_2O_3$ or $ZrO_2$—MO, wherein M is Yb, Gd, Nd, Ca, Y, Mg and Hf), bismuth oxide ($BiO_2$—$M_2O_3$, MO or $M_2O_5$, wherein M is Y, Gd, Nb, W, Sr, Ba) and ceria oxide ($CeO_2$—$M_2O_3$ or $MO_2$, wherein M is Y and Sm) can be applicable as a solid electrolyte.

A solid electrolyte is designed as a separative wall structure enabling the separation of the test gas for the detection of NOx and air having a constant atmosphere or a structure different from a separating wall structure such as a plate or rod shape may be used. In the case that a solid electrolyte is a separation wall, at least a pair of electrodes is formed at both sides of the separation wall and in the case that it is not a separation wall, at least a pair of electrodes is formed at any place of a solid electrolyte.

An electrode composed of a Group 6b metal or a material containing these oxides is coated on a solid electrolyte by screen printing, etc. and formed by sintering. A physical or chemical vapour phase deposition method such as vacuum deposition, sputtering, laser ablation, ion beam deposition and an ion plating or chemical deposition method such as a plasma chemical vapour phase deposition method can be used for the formation. The electrode formation by these methods can be done either of a metal, nitride and carbide formed beforehand under oxygen or oxygen containing atmosphere or directly by controlling the atmosphere at the formation.

The method of formation of an electrode is not limited to the above mentioned methods and any method can be used so far as the method can form an electrode composed of an oxide of a Group 6b metal or a substance containing these oxides. Furthermore, conductive material, such as laminated or plugged noble metals like Au and Pt and metals, can be formed and used as a collector.

The second electrode is composed of a noble metal such as Pt, Ag, Au and Pd, a conductive ceramic, for example, an oxide expressed by $ABO_3$ having perovskite type structure such as $LaCoO_3$, $LaNiO_3$, $LaFeO_3$ and $LaMnO_3$, and oxides, wherein a part of A or B site is replaced by an element like Sr or oxides having $K_2NiF_4$ type structure such as $La_2CuO_4$.

A sensor according to this invention is composed not only of a pair of electrodes, but also can be composed of a third electrode, for example a carbonate electrode for the detection of $CO_2$ or CO gas and a sulfate electrode for the detection of SOx gas, for the detection of other gases or removal of the effect of coexisting gases.

In a structure, wherein both of the paired electrodes are exposed in the gas without being separated by a solid electrolyte wall, NOx in the gas is detected by the measurement of the electromotive force caused by the difference in the reaction of NOx on the first electrode comprising metal oxides or a substance containing these oxides and the second electrode consisting of noble metals or electroconductive ceramics. Particularly, in this structure, it is possible to make a sensor wherein the electromotive force between the first and second electrodes does not change, even when the oxygen content in the gas changes, by the adoption of a electrode material such as Pt, which causes a 4 electron oxygen reaction at the second electrode. This is due to the fact that there is no difference in the chemical potential for oxygen at the first and second electrodes. That is, the chemical potential of oxygen at each electrode is equal because they are exposed to the same atmosphere, although both electrodes respond to oxygen.

In an electromotive force type sensor composed of a pair of electrodes formed on a solid electrolyte to detect electropotential caused by the difference of the chemical potential between the electrodes, a solid electrolyte of a transport number close to 1 is used and mixed conductive materials both for ions and electrons are not preferred. In paired electrodes formed on a solid electrolyte, the first electrode functioning as a detecting electrode reacts with the test gas existing around the surface of the electrode and the electromotive force is caused by the change of the chemical potential of the ion conductive carrier of a solid electrolyte against the chemical potential of the other electrode. Many kinds of reactions on the first electrode of an NOx sensor according to the present invention are conceivable. For example, a selective catalytic activity and oxidation/reduction for the reaction with test gas is thought to be effective for the change of chemical potential. At present the reaction on the first electrode has not been elucidated, however, the electromotive force seems to be caused by the oxidation and reduction reaction on the metal oxide.

In any of this kind sensor, a heater can be equipped for heating the sensor to a predetermined temperature.

As explained above, the melting point and decomposition temperature of metal oxides are higher than that of nitrates and metal oxides can be used as the electrode material of an NOx sensor which is exposed to an exhaust gas of several hundreds ° C. or used at a high temperature. These oxides are not water soluble and therefore, are stable in a atmosphere containing water vapour. From above view points, the inventors have prepared a sensor, wherein the first electrode on a solid electrolyte is composed of an oxide of a Group 6b metal or a substance containing these oxides and confirmed that it constitutes a NOx sensor having a good response to both $NO_2$ and NO.

EXAMPLE

The present invention will be explained according to the attached figures.

Example 1

FIG. 1 shows a cross section of an NOx sensor of Example 1 according to the first example of the present invention. A solid electrolyte of this example can be any one of zirconia, bismuth oxide and silica oxide, however, zirconia wholly or partially stabilized by yttria, calcia, silica or magnesia is preferred. A solid electrolyte is composed of zirconia tube 1 closed at one end and stabilized by magnesia. At the outside of zirconia tube 1, the first electrode 2 composed of oxides of a Group 6b metal, a collector 4 and a lead part 5 are connected. In the inside of zirconia tube 1, the second and third electrodes are prepared and connected with a lead 6. NOx concentration in the test gas is detected by the measurement of the potential difference between leads 5 and 6 by only contacting the outside of stabilized zirconia tube 1 with the test gas. The changes of electromotive force of a sensor coated with the paste of oxide powders of Cr, Mo and W sintered at 500~700° C. in an atmosphere of 21% oxygen containing 100 ppm $NO_2$ and 500 ppm NO are shown in Table 1 taking the electromotive force in the atmosphere of 21% oxygen as a reference. A sensor wherein an oxide of Cr and Mo is used in the first electrode showed a response of increased electromotive force to $NO_2$ and decreased electromotive force to NO and a sensor wherein oxide of W is used in the first electrode showed a response of decreased electromotive force both for $NO_2$ and NO.

Figure 2:
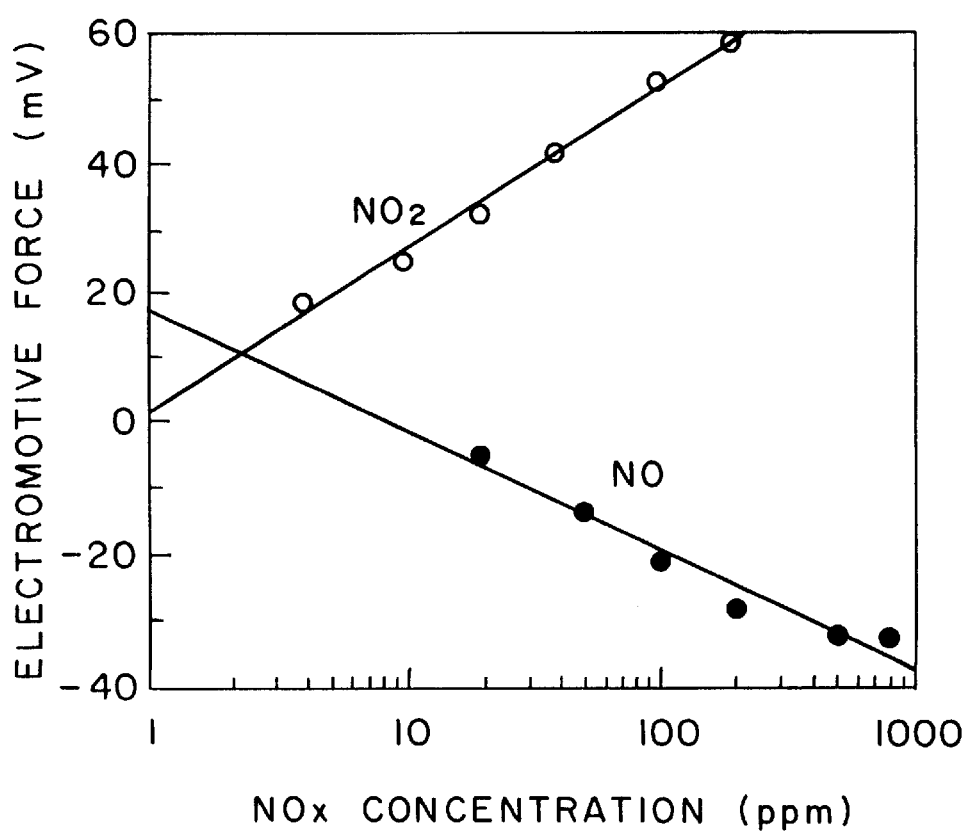
FIG. 2 shows the dependency of the electromotive force on NOx concentration in an example of NOx sensor according to the present invention.

NOx concentration dependency of the electromotive force of a sensor using Mo oxide as the first electrode at 500° C. in air is shown in FIG. 2. The electromotive force of the sensor changes in proportion to $NO_2$ and NO gas concentration. The electromotive force increases as the concentration of $NO_2$ increases and decreases as the concentration of NO increases. The sensor of this example worked at 400~600° C. and showed a change of electromotive force corresponding to the change of NOx gas concentration.

TABLE 1

The Change of the Electromotive Force corresponding to 100 ppm $NO_2$ and 500 ppm NO

| Electrode Material | The Change of the Electromotive Force (mV) | |
| --- | --- | --- |
| | 100 ppm $NO_2$ | 500 ppm NO |
| $Cr_2O_3$ | 41.3 | −28.9 |
| $MoO_3$ | 44.1 | −60.0 |
| $WO_3$ | 125.3 | 37.9 |

Example 2

Sensor of the same constitution as that of example 1 was prepared by coating a solid electrolyte with a mixture of oxide of Cr and titania, of an oxide of Mo and gold and of an oxide of Cr and an oxide of Mo and sintering thereof at 500~700° C. Oxides of Cr and Mo are detected by X-ray diffraction in the first electrode after sintering. The changes of electromotive force in the atmosphere of 21% oxygen containing 100 ppm $NO_2$ and 500 ppm NO are shown in Table 2 taking the electromotive force in the atmosphere of 21% oxygen as a reference. The sensors in this example showed a good response of increased electromotive force for $NO_2$ and decreased electromotive force for NO.

As is clear from this example, the function of an electrode almost does not depend on the ratio of the compositions of the mixture with oxides or noble metals such as Au and Pt, so far as oxides of metals of Group 6b exist.

TABLE 2

The Change of the Electromotive Force corresponding to 100 ppm $NO_2$ and 500 ppm NO

| Electrode Material | The Change of the Electromotive Force (mV) | |
| --- | --- | --- |
| | 100 ppm $NO_2$ | 500 ppm NO |
| $Cr_2O_3 + TiO_2$ | 33.4 | −26.2 |
| $MoO_3 + Au$ | 43.8 | −58.8 |
| $Cr_2O_3 + MoO_3$ | 39.5 | −33.6 |

Example 3

Figure 3:
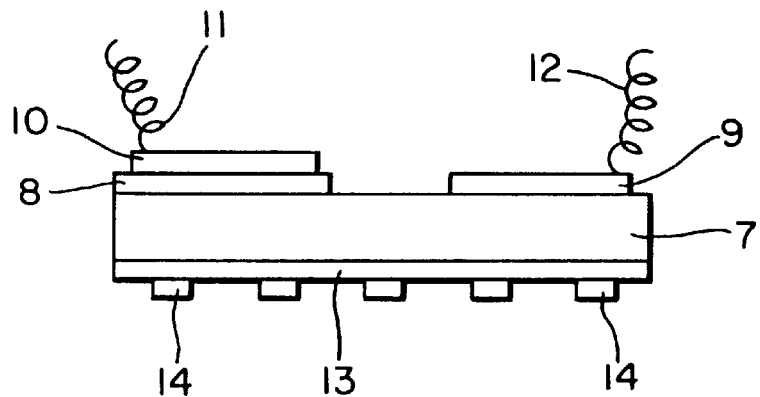
FIG. 3 shows a cross section of another example of NOx sensor of the present invention.
Figure 4:
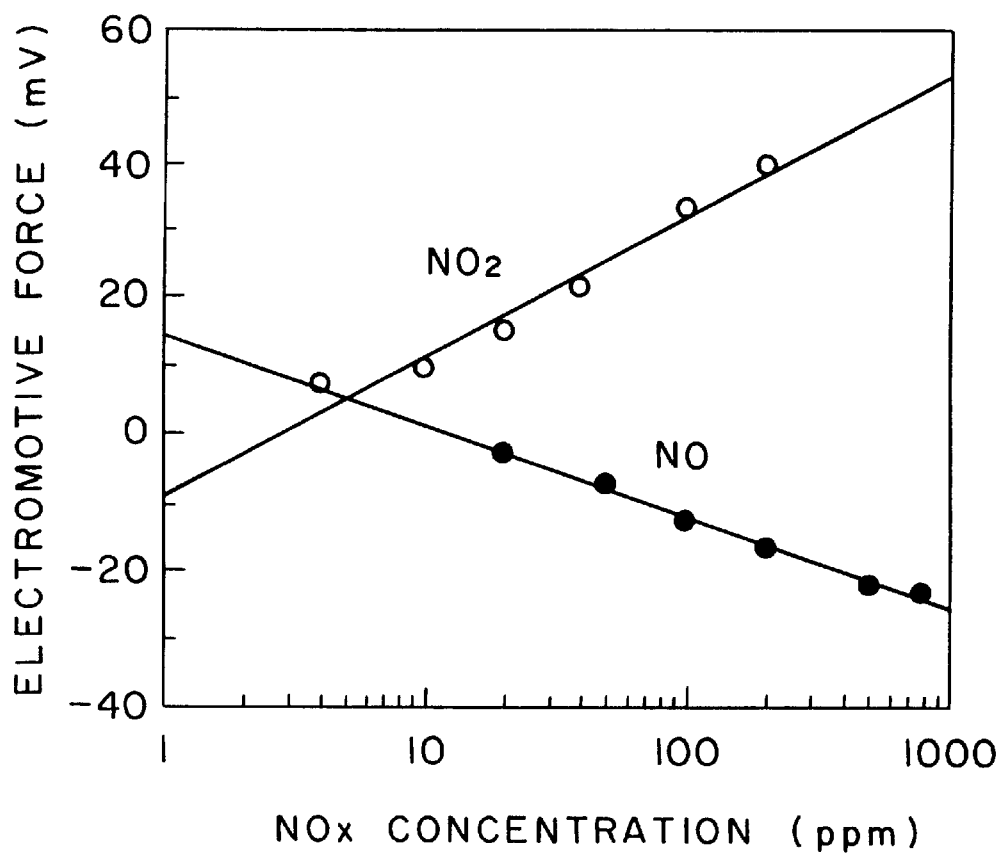
FIG. 4 shows the dependency of the electromotive force on NOx concentration in an example of an NOx sensor according to the present invention.
Figure 5:
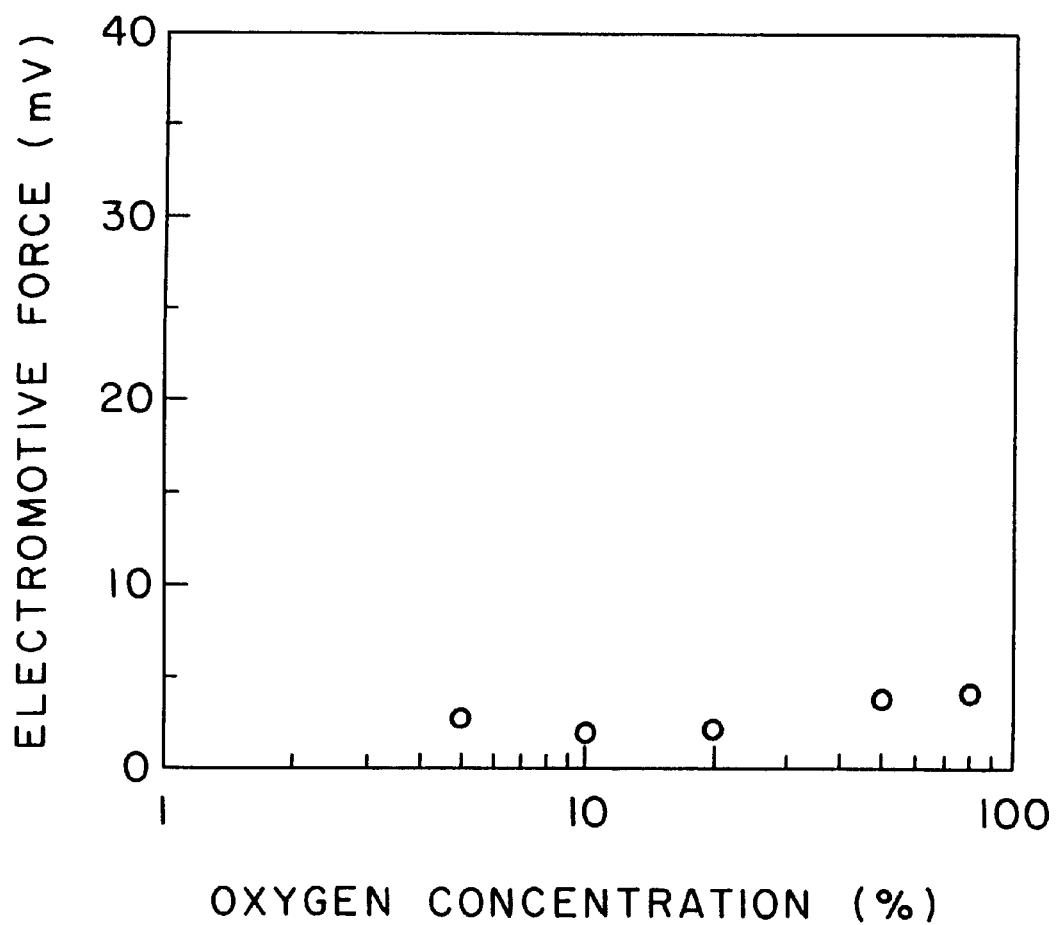
FIG. 5 shows the dependency of the electromotive force on oxygen concentration of an example of an NOx sensor according to the present invention.

FIG. 3 is a cross section of an NOx sensor of another example of the present invention. A solid electrolyte 7 is composed of zirconia stabilized by yttria. On one side of plate shaped solid electrolyte 7, the first electrode 8 and the second electrode 9 are prepared. The first electrode 8 is coated by a paste made of powder of oxide of Cr. The second electrode 9 is composed of an electrode which does not respond to NOx, in this case, Pt. The first electrode 8 and the second electrode 9 are so called gas electrodes and are porous electrodes. On the first electrode, a collector 10 made of Au is prepared and the leads 11 and 12 of the first electrode 8 and the second electrode 9 are connected with a measurement circuit.

On the opposite side of a solid electrolyte the where above electrodes are prepared, a heater 14 is prepared through insulating layer 13.

The shape of a solid electrolyte 11 is not always necessary to be a plate, but can be cylindrical one, a thin film prepared by sputtering or a thick film prepared by printing. Furthermore, the pattern shape is not limited to a particular shape.

The dependency of electromotive force on $NO_2$ concentration in the atmosphere of air at 500° C. is shown in Table 4. In this sensor, the electromotive force changes in proportion to the logarithm of the concentration of $NO_2$ and NO and increases as the concentration of $NO_2$ increases and decreases as the concentration of NO increases. Furthermore, it was confirmed that the electromotive force does not change by the change of oxygen concentration and is not affected by the oxygen concentration.

As many apparently widely different embodiments of the present invention can be made without departing from the spirit and scope thereof, it is to be understood that the invention is not limited to the specific embodiments thereof except as defined in the appended claims.

What is claimed is:

1. A method of detecting nitrogen oxide concentration in a gas which comprises:

providing a nitrogen oxide sensor comprising
a solid electrolyte substrate; a single pair of electrodes, a first electrode of said pair of electrodes formed on one side of said substrate and a second electrode of said pair of electrodes formed on another side of said substrate, and a conductor formed on said first electrode; wherein said first electrode consists of a metal oxide of a metal selected from Group 6b, or a mixture of these metal oxides, and said second electrode consists of a noble metal or a conductive ceramic;

exposing said first electrode to a first gas which contains a nitrogen oxide and oxygen and exposing said second electrode to a second gas which contains at least oxygen, wherein concentration of nitrogen oxide in said first gas is detected by converting an amount of nitrogen oxide concentration into an electromotive force level between the first and second electrodes wherein the electromotive force linearly increases in response to an increase, in terms of a logarithm, of $NO_2$ concentration and linearly decreases in response to an increase, in terms of a logarithm, of NO concentration; and measuring the nitrogen oxide concentration in said first gas by determining the electromotive force between said first and said second electrode.

2. A method of detecting nitrogen oxide concentration in a gas containing oxygen which comprises:

providing a nitrogen oxide sensor comprising
a solid electrolyte substrate; a single pair of electrodes, a first and second electrode of said pair of electrodes formed on a same side of said substrate, and a conductor formed on said first electrode; wherein said first electrode consists of a metal oxide of a metal from Group 6b, or a mixture of these metal oxides, and said second electrode consists of a noble metal or a conductive ceramic;

exposing both of said electrodes to a same gas including a nitrogen oxide and oxygen, wherein concentration of nitrogen oxide in said gas is detected by converting an amount of nitrogen oxide concentration into an electromotive force level between the first and second electrodes wherein the electromotive force linearly increases in response to an increase, in terms of a logarithm, of $NO_2$ concentration and linearly decreases in response to an increase, in terms of a logarithm, of NO concentration; and measuring the nitrogen oxide concentration in said same gas by determining the electromotive force between said first and said second electrode.

* * * * *